US010041928B2

(12) United States Patent
Berman

(10) Patent No.: US 10,041,928 B2
(45) Date of Patent: Aug. 7, 2018

(54) CONCRETE MIXTURE MEASUREMENT SENSOR, SYSTEM AND METHOD

(71) Applicant: Dully Katzeff-Berman, Saint Lazare (CA)

(72) Inventor: Berthold Berman, Saint Lazare (CA)

(73) Assignee: GCP APPLIED TECHNOLOGIES INC., Cambridge, MA (US)

( * ) Notice: Subject to any disclaimer, the term of this patent is extended or adjusted under 35 U.S.C. 154(b) by 174 days.

(21) Appl. No.: 14/760,269

(22) PCT Filed: Jan. 10, 2014

(86) PCT No.: PCT/IB2014/000024
§ 371 (c)(1),
(2) Date: Jul. 10, 2015

(87) PCT Pub. No.: WO2014/108798
PCT Pub. Date: Jul. 17, 2014

(65) Prior Publication Data
US 2015/0355160 A1    Dec. 10, 2015

Related U.S. Application Data

(60) Provisional application No. 61/751,663, filed on Jan. 11, 2013.

(51) Int. Cl.
*G01N 33/38* (2006.01)
*G01N 11/00* (2006.01)
(Continued)

(52) U.S. Cl.
CPC .......... *G01N 33/383* (2013.01); *B28C 7/024* (2013.01); *G01N 11/00* (2013.01); *G01N 11/14* (2013.01);
(Continued)

(58) Field of Classification Search
CPC ................. G01N 11/14; G01N 11/142; G01N 2011/147; G01N 2011/002;
(Continued)

(56) References Cited

U.S. PATENT DOCUMENTS 3,129,928 A * 4/1964 Huntington ............. B28C 7/024
137/92
3,147,612 A    9/1964 Evans
(Continued)

FOREIGN PATENT DOCUMENTS

EP         0924040       6/1999
EP         19308728      7/2003
(Continued)

OTHER PUBLICATIONS

Notification of Transmittal of the International Search Report and the Written Opinion of the International Searching Authority, or the Declaration.

*Primary Examiner* — Eric S McCall
*Assistant Examiner* — Mohammed E Keramet-Amircola
(74) *Attorney, Agent, or Firm* — James Ray and Assoc. IP LLC; Craig K. Leon

(57) ABSTRACT

A sensor measures slump and rheological characteristics of the concrete and is connected to a system that adjusts the slump by monitoring the sensor within the interior surface of a concrete mixer and controlling liquid additions. Data is analyzed by a computer processing unit to determine the slump and rheological characteristics of the concrete, liquid required to meet the slump requirements. The measurement done by the sensor is more accurate then the existing methods because it brings into consideration the effect of the helix inside the mixer on the movement of the concrete mixture inside the mixer. Furthermore, this method also allows the operation of the sensor in "real" life situations where the rotation speed of the mixer can't be maintained at (Continued)

a fixed value. The fact that the sensor rotates with the drum and that the concrete mixture is pushed to the bottom of the mixing drum guaranties that all the concrete is "sampled" by comparing results collected from each revolution of the mixing drum.

14 Claims, 13 Drawing Sheets

(51) Int. Cl.
*G01N 27/04* (2006.01)
*B28C 7/02* (2006.01)
*G01N 11/14* (2006.01)

(52) U.S. Cl.
CPC ... *G01N 27/048* (2013.01); *G01N 2011/0046* (2013.01)

(58) Field of Classification Search
CPC ......... G01N 2203/0676; G01N 33/383; G01N 11/00; G01N 27/048
USPC .............................................. 73/54.03, 54.28
See application file for complete search history.

(56) References Cited

U.S. PATENT DOCUMENTS

| | | | |
|---|---|---|---|
| 3,631,712 A | | 1/1972 | Mercier |
| 3,640,121 A | | 2/1972 | Mercier |
| 3,753,373 A | * | 8/1973 | Brown ............... G01K 7/34 323/364 |
| 4,335,966 A | | 6/1982 | Rapp et al. |
| 4,900,154 A | * | 2/1990 | Waitzinger .......... B28C 7/024 366/40 |
| 8,311,678 B2 | | 11/2012 | Koehler et al. |
| 9,429,559 B2 | * | 8/2016 | Radjy ............... G01N 33/383 |
| 2009/0171595 A1 | | 7/2009 | Bonilla Benegas |
| 2011/0029134 A1 | | 2/2011 | Hazrati et al. |
| 2011/0077778 A1 | * | 3/2011 | Berman ............... B28C 7/02 700/265 |
| 2012/0204625 A1 | * | 8/2012 | Beaupre .............. B28C 7/024 73/54.31 |

FOREIGN PATENT DOCUMENTS

| | | |
|---|---|---|
| EP | 2486385 | 8/2012 |
| JP | 6269142 | 3/1987 |

\* cited by examiner

CONCRETE MIXTURE MEASUREMENT SENSOR, SYSTEM AND METHOD

FIELD OF THE INVENTION

The present invention relates, in general, to concrete mixing and, more particularly, this invention relates to a system and a method for measuring of at least one of volume, water cement ratio, consistency, temperature and slump, and also to the control of slump and, yet more particularly, the instant invention relates to improved sensors for measuring at least one of volume, water cement ratio, consistency, temperature and slump.

BACKGROUND OF THE INVENTION

Concrete production like the production of any other man made material produced in batches requires a consistent repeatability of the properties of the product from batch to batch and even in the same batch. In the concrete manufacturing process it is extremely important to know that the properties haven't changed prior to pouring the concrete mixture.

It is generally well known that all tests performed on a fresh concrete mixture will indicate the future properties of the hardened concrete.

The industry testing standard for slump for example is found in ASTM C143 and is based on filling a cone with concrete mixture and measuring the slump of the concrete mixture as the cone is pulled out. Slump generally increases with water content of the concrete mixture or the addition of chemicals. During the concrete manufacturing process, the main problem is a control the accurate quantity of the water since water can be present in the aggregates and the measurement of the moisture percentage is not accurate. Having a mechanism to determine the water cement ratio before the concrete mixture is poured reduces the uncertainty of the quality and variation of the qualities of the product which is a part of the production process.

It is known that sensors can be used in the mixing of concrete. For example U.S. Pat. No. 6,484,079 issued to Buckelew et al. provides a global positioning satellite receiver to monitor the location of mixers. Similarly, U.S. Pat. No. 5,713,663 issued to Zandberg et al. measures the torque applied on the mixer in order to rotate it. U.S. Patent Publication Number 2012/0204625 to Beaupre et al. provides a probe that include a base and a resistance member extending from the base and onto which a resistance pressure is imparted by a rheological substance when the resistance member is submerged and moved therein. The resistance member includes an inner member and an outer member that surrounds the inner member and has a load cell connection therewith. Rheological properties can be obtained using values indicative of the resistance pressure both in a low speed range and in a high speed range. European patents EP1961538A2 and EP0924040 measure the pressure applied on a blade or on a cylinder shaped sensor attached to the wall of the truck mixer as the mixer rotates and the sensor is dragged against the concrete mixture. Zandberg et al. '663 is problematic since there are many factors that influence the torque. Accordingly, the torque measurement is not an adequate measure of the condition of the concrete mixture or slump. Also, due to fact that the stress has to be measured in one rotation speed only, important information is not measured because the concrete mixture moves in two axes, one axis being parallel to the rotation of the mixer's drum and the other axis being disposed at an angle to the first axis, by being vertical to the rotation of the mixer. Movement of the concrete mixture along the second axis is caused by the helix inside the mixer. To the best knowledge of the inventor, the previous inventions do not measure a component of a force along the second axis.

It has been found that the existing approach does not produce as good an approximation of the desired slump and does not provide the necessary information to estimate the amount of concrete mixture in the mixer or the start and finish times of the pour. Other approaches are based on installing a blade and measure the stress applied on the blade by the moving concrete mixture while the mixer drum is rotating. However, these solutions are problematic due to the concrete buildup behind the blade that, due to deterioration, affects the accuracy of the readings after some time.

Therefore there is a need to improve measurement of the concrete mixture at variable speeds.

All existing conventional applications are based on measuring the force and or the pressure applied by the concrete mixture onto the probe/sensor that is attached to the inner wall of the mixer drum while the mixer drum is rotating and the sensor is dragged through the concrete mixture.

It has been found that existing probes/sensors need to measure the average pressure/force that is applied on the probe/sensor by the movement of the concrete mixture, however, differentiating between a true measurement and the noise has been very challenging. Furthermore, it has been found that existing probes/sensors are also prone to extensive wear due to these reasons: high abrasion created by the aggregates, corrosive materials inside the concrete mixture and alkaline water. Therefore, there is an additional need to protect the sensor body from excessive wear.

SUMMARY OF THE INVENTION

The present invention provides a sensor and a system to measure the consistency of the aggregate concrete mixture inside the mixer and measure the rheological properties of the aggregate concrete mixture inside the mixer.

In the conventional mixing process, the mixer is required to idle and count the mixer revolutions to attempt to achieve a consistent mix. The present invention allows the user to charge the mixer and leave the yard, monitoring of the slump over several revolutions, the deviation from the average will indicate if the material is well mixed, the lower the deviation is the better the mix is mixed.

The improvement measures the stress in two axes, one parallel to the rotation of the mixer and one vertical to the rotation of the mixer and being generally perpendicular to the first axis. The force on the second axis is caused by the movement of the mixing fin or blade within the rotating mixer drum. A sensor is attached to or through the mixer and the sensor has strain gauges or load cells positioned on the sensor in the two axes. Preferably, two strain gauges are positioned on each axis, although one strain gauge on each axis is also applicable.

At least one sensor is provided with strain gauges installed on the axis in parallel to the rotation direction and a second set of strain gauges installed on the axis vertical to the rotation direction. Measuring the resistance of the strain gauges will provide a force applied on the sensor by the movement of the concrete in the direction of the strain gauges.

Rheological characteristics such as viscosity and yield stress can be calculated by using the Bingham model.

The invention also provides a dual layer cover for the sensor. The outer layer is a hard material, such as metal, that resists the movement of the concrete. A second layer made of a soft material, such as an elastomeric material, between the outer first layer and the sensor body.

The invention protects the sensor body from the harsh environment of the mixer, the service period of the sensor is increased because the first layer and/or the second layer can be replaced without replacing the sensor.

The invention also provides a sensor with a sensor body manufactured from an electrically non-conductive material and electrodes that are manufactured from an electrically conductive material and that are mounted either on a surface of the sensor body or within an interior thereof.

The present invention also provides an apparatus and method configured to measure the consistency of the aggregate concrete mixture inside the mixer; measure the consistency of the aggregate concrete mixture between different batches; measure the volume of the aggregate concrete mixture inside the mixer; measure the rheological properties of the aggregate concrete mixture inside the mixer; and measure the water cement ratio of the aggregate concrete mixture inside the mixer.

OBJECTS OF THE INVENTION

It is, therefore, one of the primary objects of the invention to provide an improved apparatus and method to control and monitor concrete mixing in a rotating mixer.

Another object of the invention is to provide an improved apparatus to monitor slump and rheological characteristics of concrete in the rotating mixer.

Still another object of the invention is to provide an improved apparatus to record the consistency of the concrete mixed during preparation and pour.

Another object of the invention is to provide a concrete mixing control apparatus according wherein one or more sensors are attached to the interior surface of the rotating mixer.

Another object of the invention is to provide a concrete mixing control apparatus wherein the valve is operatively connected to the computer processing unit and controlled by the computer processing unit.

Another object of the invention is to provide a concrete mixing control apparatus further having an input means operatively connected to the computer processing unit to enter one or more of the requested slump, mix and customer information.

Another object of the invention is to provide a concrete mixing control apparatus wherein the input means is one of a touch screen, voice recognition, keyboard and alphanumeric keypad.

Another object of the invention is to provide a concrete mixing control apparatus wherein the input device permits the user override the data from the sensors and the computer processing unit.

Another object of the invention is to provide a concrete mixing control apparatus wherein the data storage unit is in a remote location from the concrete mixer.

Another object of the invention is to provide a concrete mixing control apparatus further includes an output means.

Another object of the invention is to provide a concrete mixing control apparatus wherein the output means is a printer.

Another object of the invention is to provide a concrete mixing control apparatus wherein the computer processing unit, input means, data storage, second display means and output means separately or in combination are in a remote location from the concrete mixer, wherein the sensors, valve and flow meter are operatively connected by a transmitter and receiver at the mixer and at the remote location.

Another object of the invention is to provide a concrete mixing control apparatus further having a global positioning satellite receiving unit having a digital output operatively connected to the data storage unit.

Another object of the invention is to provide a concrete mixing control apparatus further having a temperature sensor attached to the interior surface of the mixer operatively connected to the data storage unit.

Another object of the invention is to provide a concrete mixing control apparatus further having a moisture sensor attached to the interior surface of the mixer operatively connected to the data storage unit.

A further object of the invention is to provide a concrete mixing control apparatus further having a mixer pour valve operatively connected to the computer processing unit wherein the pour valve.

Another object of the invention is to provide a concrete mixing control apparatus wherein the computer processing unit analyses the input from the sensor to determine the start and end time the pour of concrete.

An additional object of the invention is to provide a method to control the slump of concrete comprising the following steps: charging a mixer having a drum and interior surface with particulate material; rotating the mixer drum; receiving data in a data storage unit of slump measured by the sensor; inputting at least the desired slump with an input device operatively connected to a computer processing unit further operatively connected to the data storage unit; determining the amount of liquid needed for the desired slump by the computer processing unit; and controlling the addition of liquid to the mixer through a fluid supply line in fluid communication with the mixing drum wherein the fluid supply line has a valve operatively connected to the computer processing unit and a flow meter operatively connected to the data storage unit.

Another object of the invention is to provide a method to determining the quantity of concrete mixture within the mixing drum comprising: monitoring if a sensor is submerged into the concrete within a mixing drum; rotating such mixing drum; recording the time difference between the point where the sensor is at the top and the time it is submerged within such concrete; recording the total revolution time, recording the time difference between that such sensor submerged and emerges from such concrete mixture; and calculating the volume of concrete within such mixing drum analyzing the measured periods.

Yet another object of the present invention is to provide a method to determine if the concrete mix within a mixing drum is consistent comprising: monitoring the rheological characteristics of the concrete by the sensor in the concrete per each revolution and calculating the variance between following revolutions, the lower the variance is, the better the concrete is mixed.

An object of the invention is to provide a sensor that includes a plurality of strain gauges or electrodes.

Another object of the invention is to provide a sensor that includes a protection from the harsh environment in the mixer.

Yet another object of the invention is to reduce the signal to noise ratio of the sensor.

Still another object of the invention is to increase the service life of the sensor by providing a less costly replacement of the outer layers to prolong the sensor life.

A further object of the invention is to provide an improved apparatus to monitor water/cement ratio of concrete in the mixer.

Yet a further object of the invention is to provide an improved apparatus to monitor amount of concrete poured.

Still a further object of the invention is to provide an improved apparatus to measure the long term permeability of the concrete to chloride; this also will allow the prediction of the service time of the concrete.

Still a further object of the invention is to provide an improved apparatus to record the consistency of the concrete mixed during preparation and pour.

Yet a further object of the invention is to provide an apparatus and method to record the time of beginning the pour of mixed concrete and its conclusion.

Another object of the invention is to provide a concrete mixing control apparatus comprising a concrete mixer with an interior surface and at least one sensor with electrodes to measure the electrical characteristics (resistance and impedance in various frequencies) of the concrete. Monitor the angle or the time tick in which the sensor is submerged into the concrete and the angle or the time tick in which it is emerged out of the concrete by measuring the conductivity/resistance of the concrete.

Another object of the invention is to provide a concrete mixing control apparatus having a mixer pour valve operatively connected to the computer processing unit.

Another object of the invention is to provide a concrete mixing control apparatus wherein the computer processing unit analyses the input from the sensor to determine the start and end time the pour of concrete.

Yet another object of the invention is to provide a method for determining the slump of concrete mixture within the mixing drum comprising: rotating such mixing drum; recording the angle that the sensor is submerged within such concrete; recording the angle that such sensor emerges from such concrete mixture; and calculating the slump of concrete within such mixing drum analyzing the submerge angle and emerge angle, using conversion table or a mathematical function.

Still another object of the invention is to provide a method for determining the water/cement ratio of concrete mixture within the mixing drum comprising: monitoring if a sensor is submerged into the concrete within a mixing drum; rotating such mixing drum; recording the electrical resistance of the concrete; and calculating the water/cement ratio of concrete within such mixing drum analyzing the electrical resistance.

Another object of the invention is to provide a method for determining the slump of concrete mixture within the mixing drum comprising: rotating such mixing drum; recording the time difference between the point where the sensor is at the top and the time it is submerged within such concrete; recording the total revolution time, recording the time difference between the times such sensor submerged and emerges from such concrete mixture; recording the time difference between the time the sensor emerged out of the concrete and the time it arrived to the top of the mixer; and calculating the slump of the concrete within such mixing drum analyzing the times.

Yet another object of the invention is to provide a method for determining the quantity of concrete mixture within the mixing drum comprising: monitoring if a sensor is submerged into the concrete within a mixing drum; rotating such mixing drum; recording the angle that the sensor is submerged within such concrete; recording the angle that such sensor emerges from such concrete mixture; and calculating the volume of concrete within such mixing drum analyzing the submerge angle and emerge angle.

A further object of the invention is to provide a concrete mixing control apparatus having an input from a pressure sensor mounted on the hydraulic system, analyzing the changes of the pressure with the measurement of the slump and the quantity indicates the mechanical condition of the hydraulic system, thus improving the maintenance of the hydraulic system.

In addition to the various objects and advantages of the present invention described with some degree of specificity above it should be obvious that additional objects and advantages of the present invention will become more readily apparent to those persons who are skilled in the relevant art from the following more detailed description of the invention, particularly, when such description is taken in conjunction with the attached drawing figures and with the appended claims.

BRIEF DESCRIPTION OF THE EMBODIMENTS

Figure 1:
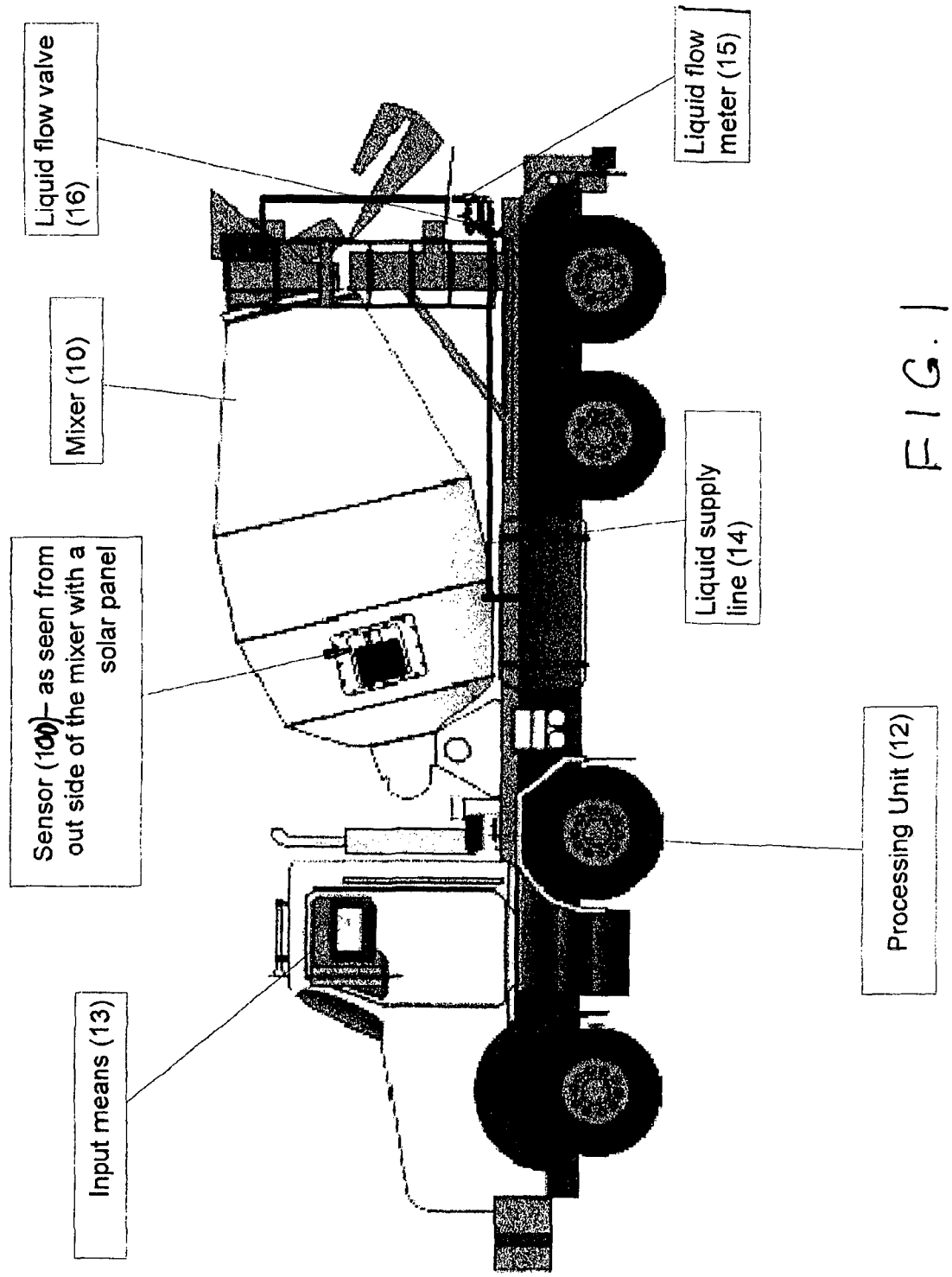
FIG. 1 is an environmental elevation view of a mixer employing a sensor of the instant invention for sensing aggregate concrete mixture.
Figure 2:
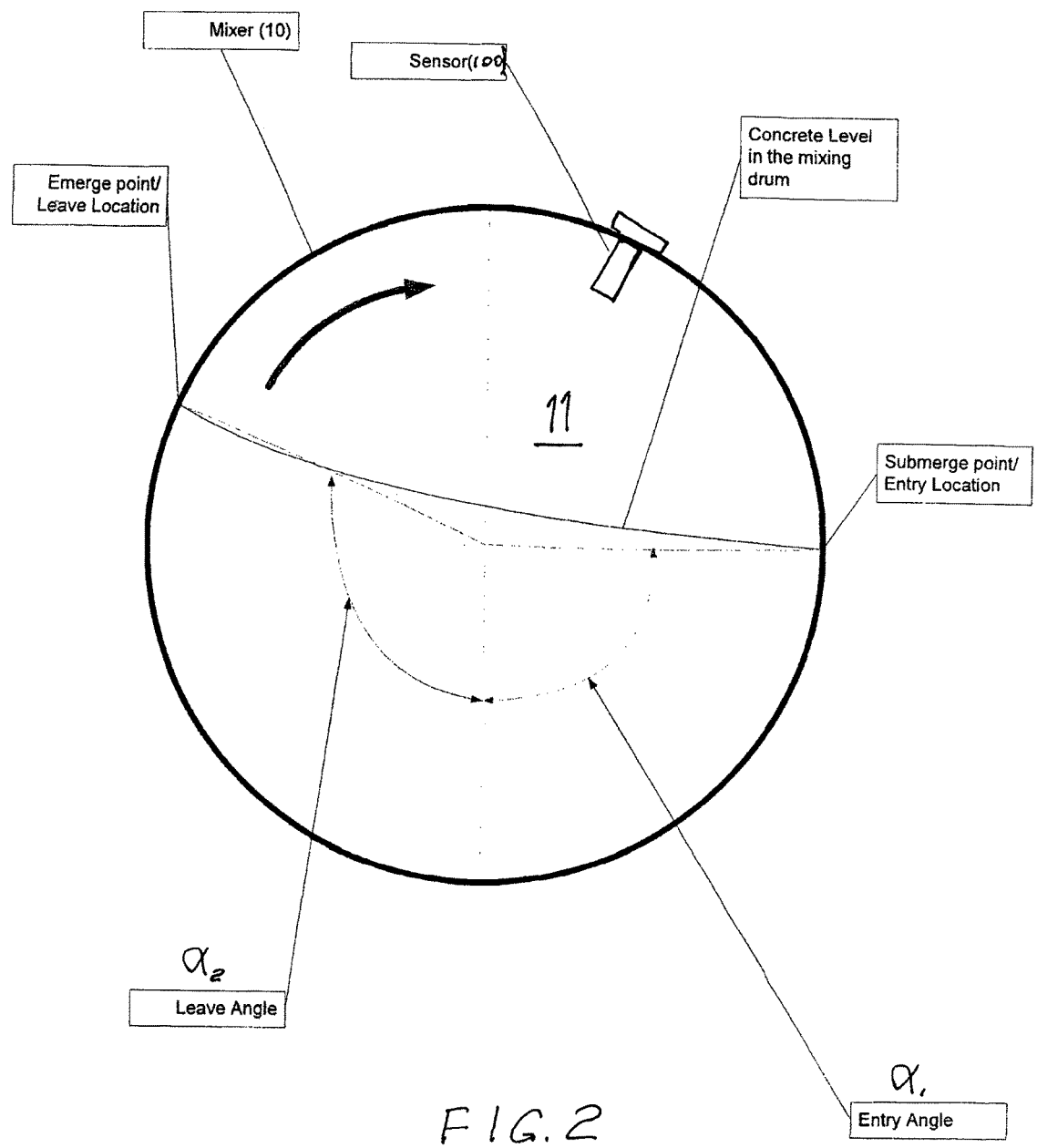
FIG. 2 is a diagrammatic view of the sensor for sensing concrete mixture within a rotating mixer of FIG. 1.

Prior to proceeding to the more detailed description of the present invention it should be noted that, for the sake of clarity and understanding, identical components which have identical functions have been identified with identical reference numerals throughout the several views illustrated in the drawing figures.

Instant invention, in accordance with one embodiment, provides an improved sensor, generally designated as 100, for a concrete mixer 10. The sensor 100 comprises a sensor body 110 and sensing elements mounted on a surface of or within the sensor body 110 and connectable to a control circuit 140.

Reference is now made, more particularly, to FIGS. 1-6, wherein a concrete mixer 10, illustrated in FIG. 1 as a conventional rotating drum, has a sensor 100 being attached to the wall of the mixer 10 so that a body 110 of the sensor 100 extends, generally radially, into the hollow interior 11 of the mixer 10. The presently preferred cross-sectional shape of the sensor body 110 is an annular ring.

Figure 3:
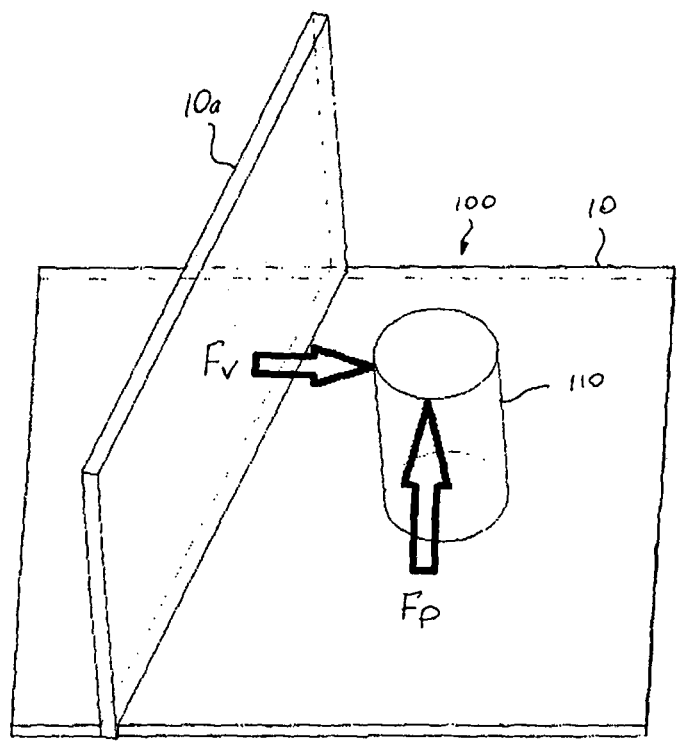
FIG. 3 is a diagrammatic view of forces acting onto the sensor of FIG. 2.

Although conventionally it has been considered that the concrete mixture applies a force onto the body 110 only in one direction being parallel to the rotation direction of the concrete mixer 10, the inventor found that the mixing drum 10 and, more particularly, the fins or blades 10a of the helix inside the mixer 10 apply a force onto the sensor body 110 along a second axis being disposed at an angle to the rotation direction of the mixer 10, as is best shown in FIG. 3.

Figure 4:
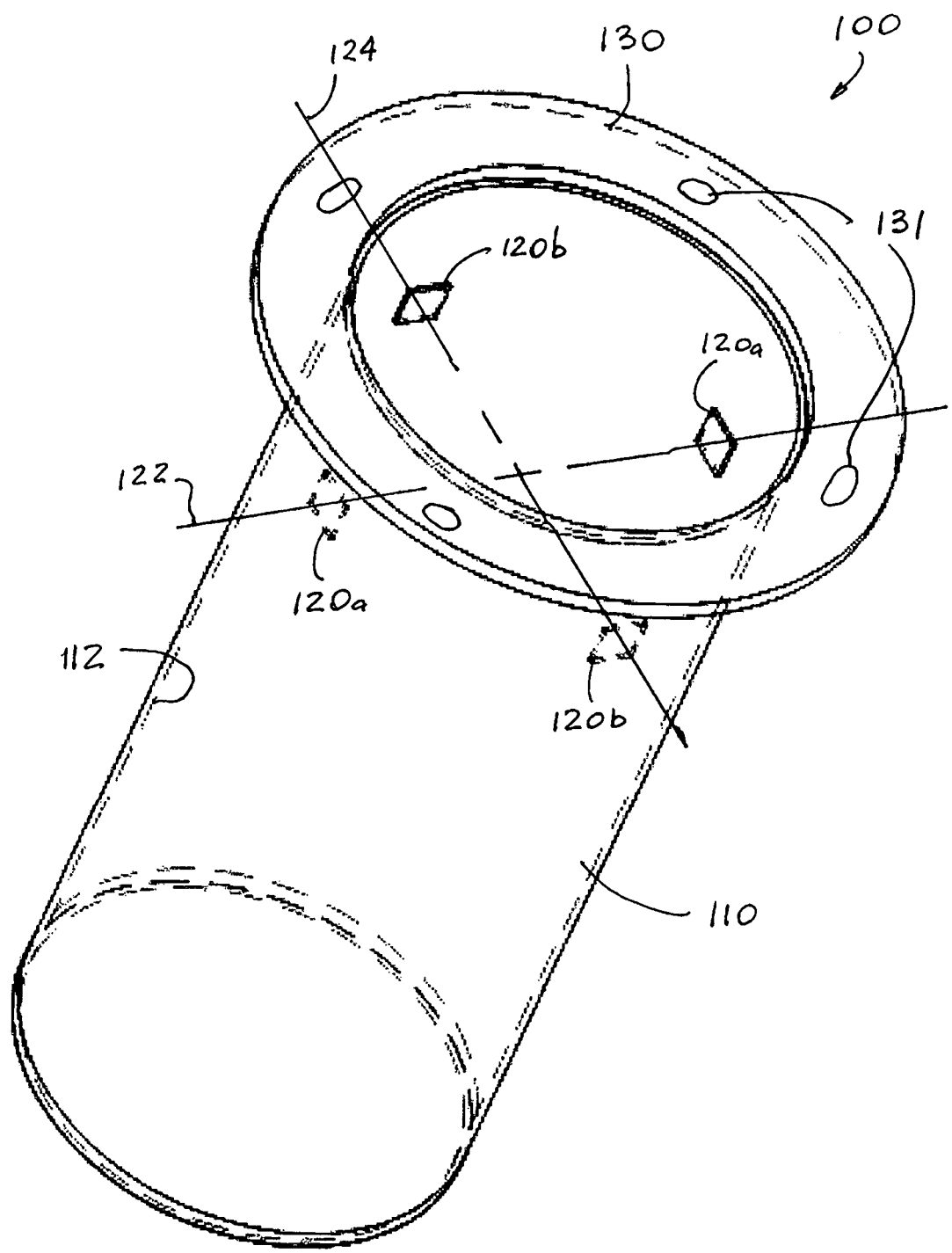
FIG. 4 is a perspective view of one embodiment of the sensor employed in FIG. 2.
Figure 5:
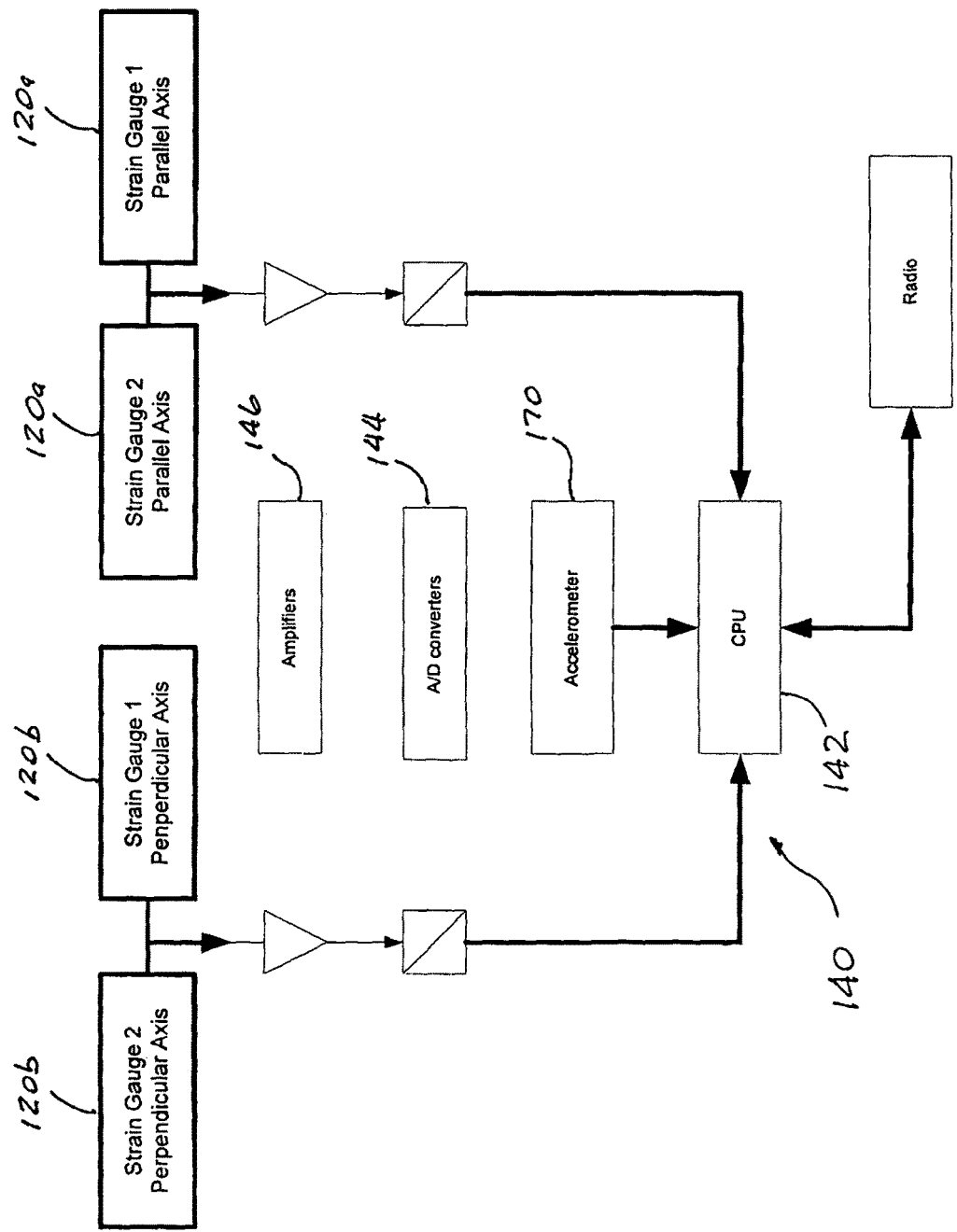
FIG. 5 is a block diagram of a control circuit employed with the sensor of FIG. 4.

Accordingly, as is best shown in FIG. 4, the body 110 is hollow, and the sensing elements includes at least two and preferably four strain gauges 120 mounted on an interior round surface 112 of the hollow sensor body 110. Two of the four strain gauges 120, referenced for the sake of clarity with numeral 120a, are mounted, mediate ends of the hollow sensor body 110, along a first axis 122 being parallel to rotation direction of the concrete mixer 10 and the remaining two strain gauges 120, referenced for the sake of clarity with numeral 120b, are mounted along a second axis 124 being disposed at an angle to the first axis 122 when the sensor 100 is attached to the wall of the concrete mixer 10. The second axis 124 is defined by a rotation of the helix fin or blade 10a within the mixer 10. Preferably, strain gauges 120a and 120b are identical to each other and could be of any conventional strain gauge type. The sensor body 110 may be attached to the wall of the mixer 10 by any conventional means and, preferably, the sensor 100 further comprises a base 130 attached, either permanently or removably, to one end of the hollow sensor body 110. The base 130 may be adapted with mounting apertures 131, so as to conventionally fasten the sensor 100 to the wall of the mixer 10, either directly or through intermediate member(s). It is to be understood, that use of the strain gauges 120a and 120b does not require a flexible connection between the sensor body 110 and the base 130 and, thus such connection is preferably a rigid connection, for example such as by welding, threaded arrangement (not shown), friction fit or by a unitary one-piece construction of the sensor body 110 and base 130, for example by a casting or a molding process.

Figure 7:
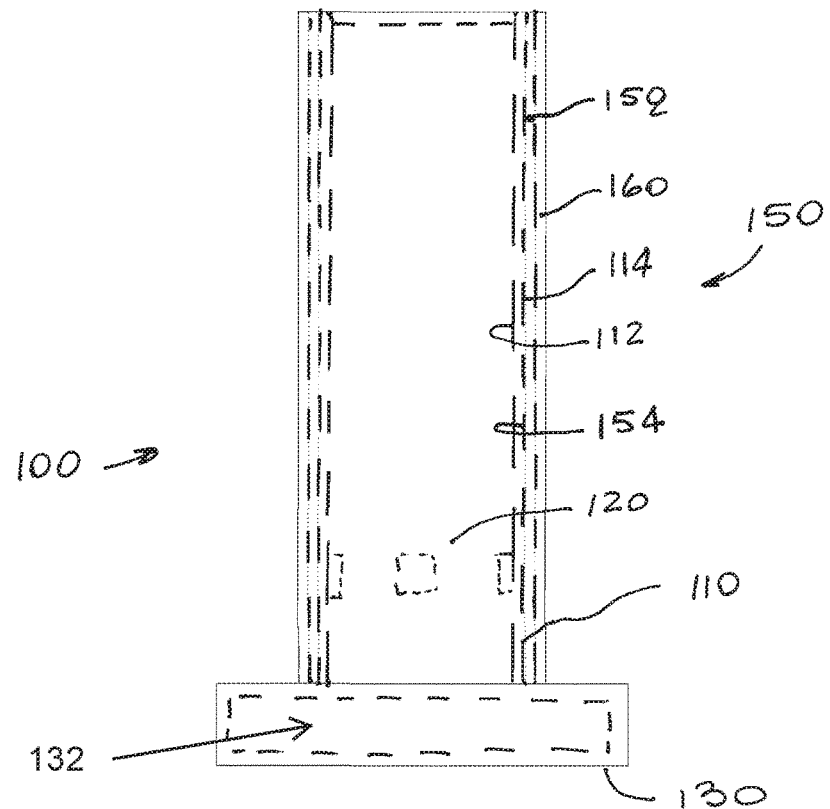
FIG. 7 is an elevation view of another form of the sensor of FIG. 4, adapted with a protective sleeve.

Preferably, the base 130 has a hollow interior 132, best shown in FIG. 7, wherein the control circuit 140 is disposed within such hollow interior 132 of the base 130 and includes a controller, preferably such as a microprocessor 142, wherein the four strain gauges 120a, 120b are connected with wires to the central processing unit (CPU) or processor 142 in a Wheatstone bridge arrangement. The control circuit 140 further includes conventional A/D converter(s) 144 and signal amplifier(s) 146, as is bet shown in FIG. 5.

In operation, measurement of the resistance of the strain gauges 120a, 120b provides forces applied onto the sensor 100 by the movement of the concrete mixture in the direction of the strain gauges 120a and in the direction of the strain gauges 120b.

Preferably, the strain gauges 120a, 120b are mounted in a close proximity to the base 130 and to the inner surface of the rotating drum 10 to take advantage of a condition wherein the sensor 100 rotates with the mixing drum 10 and wherein the concrete mixture is pushed to the bottom of the concrete mixer (mixing drum 10). Thus, positioning the strain gauges 120a, 120b in the close proximity to the base 130 improves sampling of the concrete mixture by comparing results collected from each revolution of the mixing drum 10.

Furthermore, the strain gauges 120a, 120b are only mounted on the inner surface 112 of the hollow sensor body 110 and do not require any connection with the base 130 besides the electrical connections.

By way of one example only, the total force applied onto the sensor 100 is calculated as the vector sum of both forces:
F—The total force applied onto the sensor body 100 of the sensor 100.
Fp—The force applied on along first axis 122 as measured by strain gauges 120a.
Fv—The force applied along the second axis 124 as measured by strain gauges 120b.

$$F=\sqrt{Fp^2+Fv^2}$$

The slump of the concrete mixture is directly related to the force F and can be calculated from the measured force F by several ways, including a conversion table and a mathematical equation based on the Bingham model of non-Newtonian fluids.

Rheological characteristics, such as viscosity and yield stress, can be also calculated by using the Bingham model. Additionally, calculating the variance between subsequent revolutions provides a mixing quality of the concrete mixture, wherein the lower the variance is, the better the concrete mixture is mixed.

Figure 6:
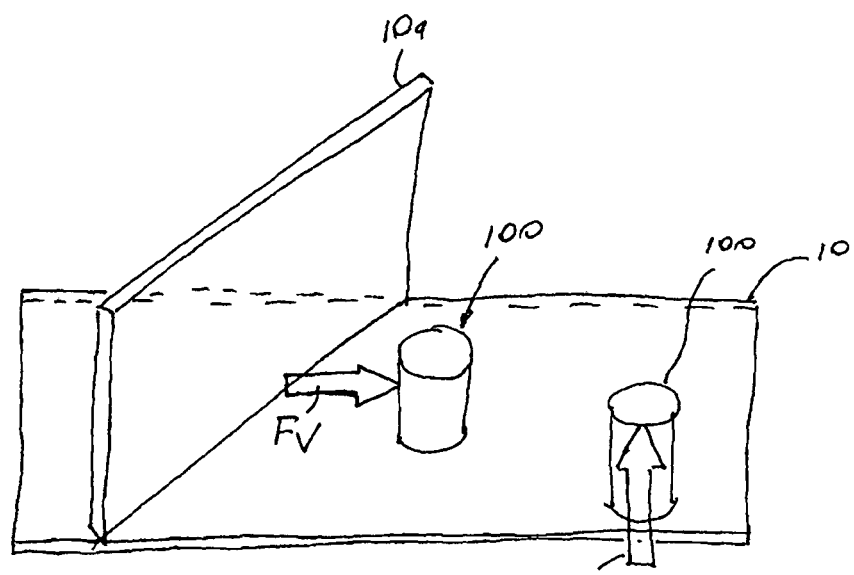
FIG. 6 is illustrates an alternative form of the sensor of FIG. 4.

Now in a particular reference to FIG. 6, the instant invention also contemplates that strain gauges 120a and 120b may be carried by separate sensors 100. More specifically, the instant invention provides two sensors 100, each containing one and preferably two strain gauges 120, wherein these two sensors 100 are oriented, at installation, such that the strain gauge(s) 120 is(are) disposed along the first axis 122 and the strain gauge(s) 120 is(are) disposed along the second axis 124.

The sensor 100, and more particularly, the control circuit 140, is operatively connected to a computer processing unit 12 via wired or wireless connection. In operation, a particulate matter as an ingredient of concrete is added to the mixer 10. The mixer 10 rotates and, as is conventional, the sensor body 110 and the sensing elements 120a, 120b are being cyclically submerged in the concrete mixer and emerge from the concrete mixture.

Now in a further reference to FIG. 1, the computer processing unit 12 is operably connected to an input means 13, preferably one of a touch screen, voice recognition, keyboard and alphanumeric keypad (not shown). The input means 13 permits the user to enter one or more of the requested slump, mix and customer information. The instant invention contemplates that the computer processing unit 12 may integrate therewithin the above described control 140.

The desired slump, mix and the customer information is entered by the user. The computer processing unit 12 determines the quantity of liquid to be added to the mixer 10 to obtain the required slump based on the measured slump and water/cement ratio, the system will assure that the water/cement ratio will not be out of the required range.

The concrete mixer 10 also has a conventional liquid supply line 14 that is attached to and in fluid communication with the concrete mixer 10 and has a liquid flow meter 15 and a valve 16 controlling the flow of liquid through the liquid supply line. The liquid flow meter 15 and valve 16 are operably connected to the computer processing unit 12. The liquid flow meter 15 is preferably disposed within the liquid supply line 14 between the valve 16 and the concrete mixer 10.

It has been found by the inventor that there is a direct relationship between the angles that the sensor 100 is submerged and emerged and the slump. Therefore, the slump can be determined through the analysis of the strain measurement in both first and second axis, 122 and 124 respectively, from the sensor(s) 100.

It has been found by the inventor that there is a direct relationship between the electrical resistance of the concrete mixture, as measured between two sensing parts of the sensor (or one electrode and the mixing drum itself) for various frequencies and the concrete water/cement ratio. Therefore, the water/cement ratio can be determined through the analysis of the resistance data as collected from the data from the sensor 100.

It has been found by the inventor that there is a direct relationship between the electrical resistance of the concrete as measured between two sensing parts of the sensor 100 (or one electrode and the mixing drum itself) for various frequencies and the concrete permeability. Therefore, the permeability can be determined through the analysis of the resistance data as collected from the data from the sensor 100.

The computer processing unit 12 also analyzes the data from the sensor 100 to determine the amount of concrete mixture within the mixer 10 by measuring the angle difference between the angle at the point that sensor 100 was submerged and the angle in which it was emerged as mixer 10 rotates and the sensor 100 moves into the cement mixture and emerges from the cement mixture. The total number of degrees that sensor 100 was submerged inside the concrete mixture indicates the level of the concrete mixture within the mixer 10. As the concrete mixture is poured out, the concrete mixture level decreases within the mixer 10. The data from the sensors 100 is used to record a change in the level of the concrete mixture and time that the level changes. The change in the quantity is the amount of the concrete mixture poured and the start and end time of the pour is recorded.

The knowledge of the remaining amount and slump of concrete in the mixture allows an adjustment in the quantities of solids and liquid to refill the mixer 10 by the user. The knowledge of the amount poured permits accurate billing to the customer. The start and finish time allow the user to deter unauthorized pours by the mixer operator.

The knowledge of the remaining amount and permeability of the concrete solids in the mixture allows an adjustment in the quantities required to refill the mixer 10 by the user.

Further, the data is stored in a data storage unit 17 operably connected to the computer processing unit 12 to allow the use of the data as received or for the later retrieval of data.

Further, a pressure sensor (not shown) installed on the hydraulic system of the truck and connected to the system will provide data on the hydraulic system's "health", since there is a correlation between the hydraulic pressure, the slump and the quantity; any change in the hydraulic pressure for the same conditions will indicate that something is wrong with the hydraulic system.

A display means preferably a computer monitor is operably connected to a computer processing unit 12. Also, an output means, preferably one of a printer, is operably connected to the computer processing unit.

Additionally, the presently preferred embodiment of the system includes a moisture sensor and temperature sensor that are operably connected to the computer processing unit 12. This additional sensors allow the user to further control the concrete mixture.

In the presently preferred embodiment, the system has a global positioning satellite receiver 30 with a digital output and a transmitter. The transmitter is operatively connected to the flow meter 15 and sensor 100 to transmit the location, stress or pressure data and flow of liquid to a remote location. The input means 13, output means, computer processing unit 12, data storage unit 17, display means and output means may separately or in combination be situated at a remote location from the mixer 10.

The moisture sensor and temperature sensor, alone or in combination with each other, are operatively connected to a sensor display 22 that is at the pour location.

The input means 13 can be used by the user to override the computer processing unit 12 and said sensors 100 to manually control the process.

The invention also contemplates use of the data measured from the sensor 100 and displayed on display 22 to control the valve 16 manually.

The method of controlling the slump, includes the step of entering the slump mix characteristics, including the maximum water to cement ratio, the requested slump and the mixer characteristics. The force on a sensor within a mixer 10 is calculated in terms of pressure or stress. The sensor output is monitored and the amount if any of additional liquid to be added to the mix is calculated. Approximately 85% to 95% of the amount of liquid is added to the mix. The mixer can then leave the plant and any additional liquid can be added at the site of the pour. The stress sensors are monitored and if the force is generally the calculated value the method in complete.

The method also contemplates use of an optional moisture sensor so as to monitor the moisture monitor and to use this data in calculating any additional liquid.

Also, there is a method to maintain the consistency of the mixture. Rather than count mixer rotations, the present invention includes a method to maintain the consistency of the mixture by monitoring the electrical characteristics, the submerged and emerge angles and comparing them over several rotations. The mixture consistency is acceptable where the sensor data varies less than a predetermined range that varies by concrete application.

Another method is provided to determine the quantity of concrete mixture within the mixing drum comprising: monitoring if a sensor is submerged into the concrete within a mixing drum; rotating such mixing drum; recording the time difference between the point where the sensor is at the top and the time it is submerged within such concrete; recording the total revolution time, recording the time difference between that such sensor submerged and emerges from such concrete mixture; and calculating the volume of concrete within such mixing drum analyzing the measured periods.

Yet another method is provided to determine if the concrete mix within a mixing drum is consistent comprising: monitoring the rheological characteristics of the concrete by the sensor in the concrete per each revolution and calculating the variance between following revolutions, the lower the variance is, the better the concrete is mixed.

Figure 8:
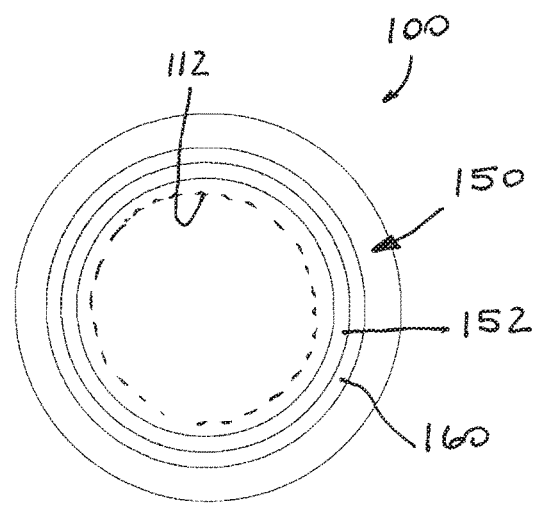
FIG. 8 is a planar end view of the apparatus of FIG. 7.

In order to improve the performance of the sensors/probes 100 and to increase their service period, a protection sleeve, generally designated as 150, is mounted onto an exterior surface 114 of the sensor body 110, as best shown in FIGS. 7-8. The protection sleeve 150 is preferably comprised of two layers, a soft material layer 152 that surrounds the exterior surface 114 of the sensor body 110 and is being manufactured from a first material, and a second layer 160 which surrounds an exterior surface of the first layer 152 and which is manufactured from a second material having a hardness thereof being greater than a hardness of the first material. The first material may be of an elastomeric type, such as rubber or the equivalent, to provide a protective layer to the sensor body 110 and dampen, cushion or absorb the shock onto the body 110 from high abrasion created by the aggregates, corrosive materials inside the concrete mixture and alkaline water and at least substantially reduce if not completely eliminate noise factor of the measurement. Such first material layer is between about ⅛ inch and about 1 inch, preferably being about inch in thickness.

The layers 152, 160 may be individually assembled onto the sensor body 110 or the sleeve 150 may be provided as a unitary, one-piece construction. In either form, it is presently preferred to size the interior surface 154 and select the durometer or hardness of the of the first layer 152 so as to allow ease of sliding the first layer of the exterior surface 114 of the sensor body 110. Then, the protective sleeve 150 can be easily replaced in the field so as to extend the service life of the sensor 100.

The hardness of the second material is sufficient to resist wear of the body 110 from contact with the aggregate concrete mixture. More specifically, the hardness of the second material is sufficient to resist a movement of the aggregate concrete mixture and allow the sensor 100 to measure rheological characteristics of the aggregate concrete mixture in a manner that substantially reduces if not completely eliminates signal/measurement noise. By way of one example only, the second material may be a metal or equivalent. The second material layer 160, which is the external layer, covers the sensing part of the sensor body 110 and is made out of a hard wear-resistant material that will resist the movement of the concrete and allow the sensor 100 to measure the rheological characteristics of the aggregate concrete mixture, if the material exposed for contact to the aggregate concrete mixture will be a soft material then the sensor 100 will measure the friction between the sensor and the concrete mixture and not the rheological characteristics. In other words, although being operable under some conditions, particularly, where the accuracy is not of a concern, the sensor 100 will not accurately measure the rheological characteristics of the aggregate concrete mixture when the soft layer 152 is not covered by the hard layer 160 due to abrasion of such layer 152 by the aggregate concrete mixture.

Figure 9:
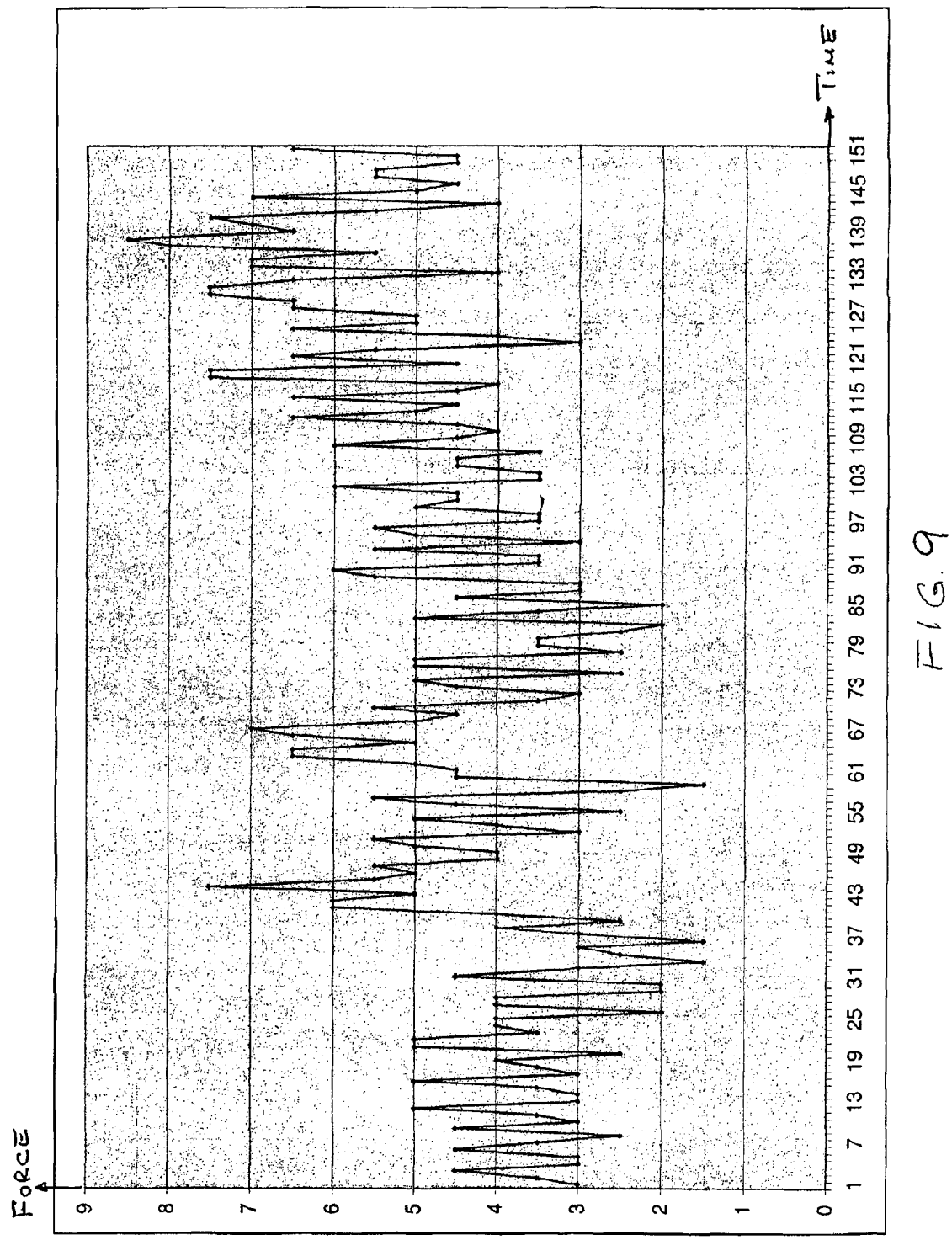
FIG. 9 is a graph of sensor output with the protecting sleeve of FIGS. 7-8.
Figure 10:
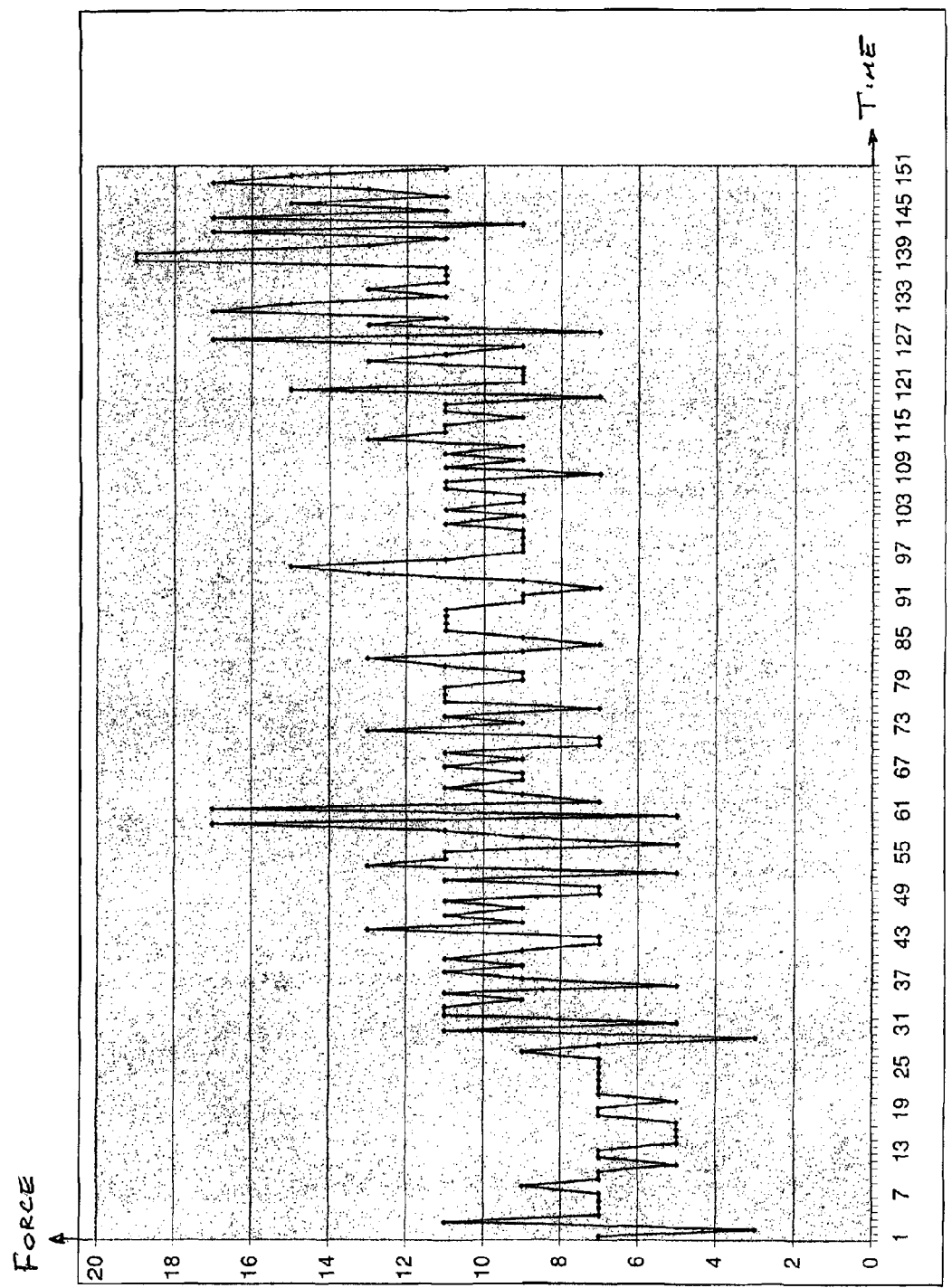
FIG. 10 is a graph of sensor output without the protecting sleeve of FIGS. 7-8.
Figure 12:
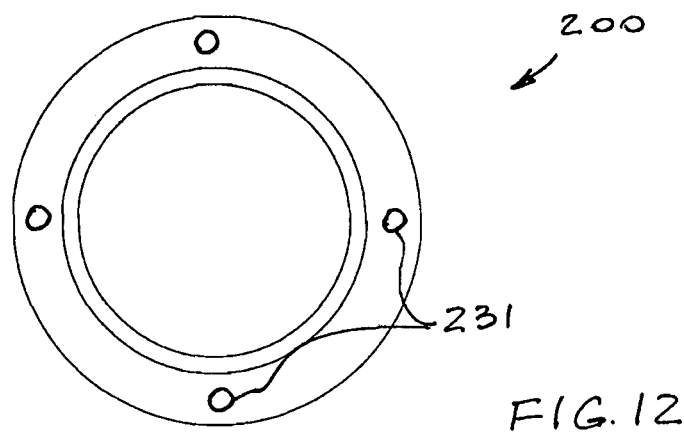
FIG. 12 is a planar end view of the apparatus of FIG. 11.
Figure 11:
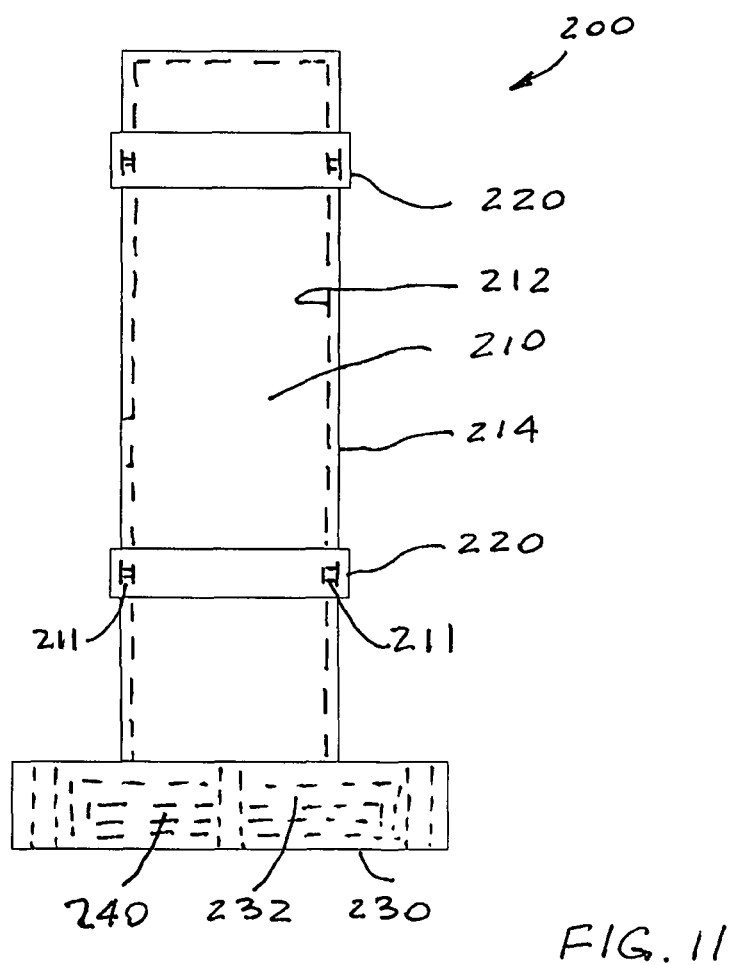
FIG. 11 is an elevation view of another embodiment of a sensor for sensing concrete mixture within a rotating mixer of FIG. 1.
Figure 14:
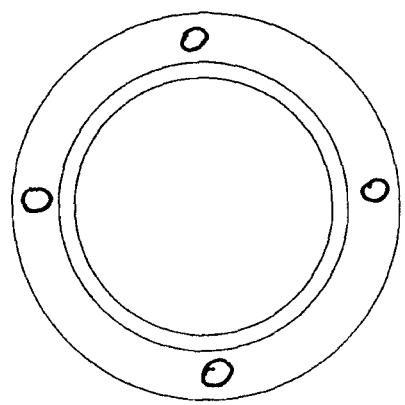
FIG. 14 is a planar end view of the apparatus of FIG. 13.
Figure 13:
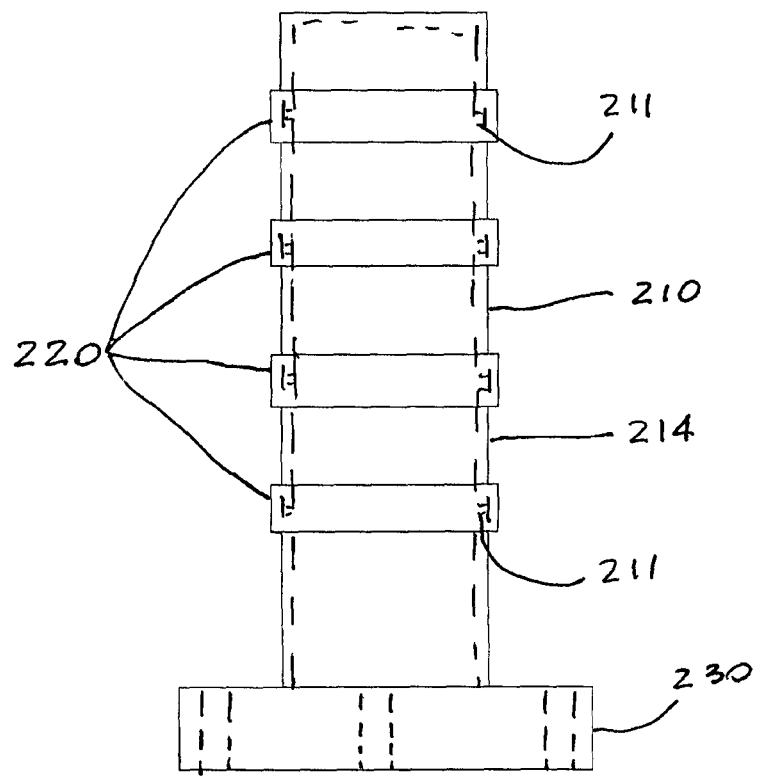
FIG. 13 is an elevation view of an alternative form of the sensor of FIG. 11.
Figure 15:
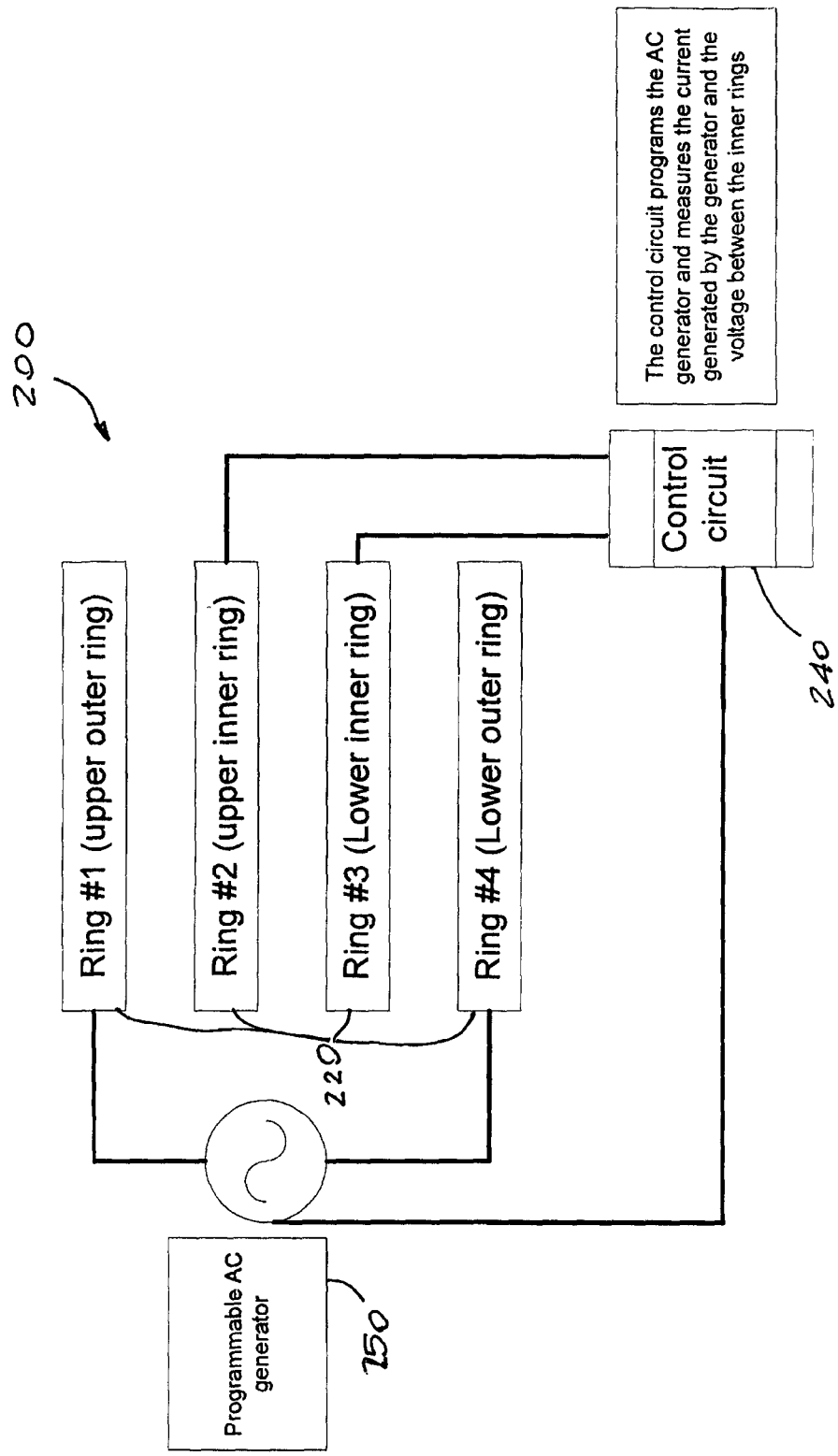
FIG. 15 is a block diagram showing connection of the sensor of FIGS. 13-14 to a control circuit.

The inventor has discovered that the combination of a first layer 152 and second layer 160 materially improves the measurement of the rheological characteristics of the concrete mixture. It has been found that the combination acts as a filter, reducing the effect of the turbulence caused by the movement of the sensor 100 through the concrete mixture. The two layered structure gives the following advantages: the sensor 100 is less prone to damages caused by the environment; the service period of the sensor 100 is increased because the sleeve 150 and/or the sensor body 110 (being removably attached to the base 130) that comes in contact with the concrete mixture can be replaced at a much lower cost than the whole sensor 100; and the readings from such sensor 100 are more reliable and easier to process due to an improved noise to signal ratio. The performance improvements are demonstrated in FIG. 9, wherein the sensor 100 is used with the sleeve 150 vs. FIG. 10, wherein the sensor 100 is employed without a sleeve 150. In both figures, vertical axis defines force and horizontal axis defines times. FIG. 9 clearly shows an improved ratio between the signal and the noise.

Although, the sleeve 150 has been described for use with the above described sensor 100, the sleeve 150 can be used to improve any existing sensor/probe design, for example, of the type as described in the U.S. Pat. Pub. Number 2012/0204625 to Beaupre et al., whose teachings are incorporated herein by reference thereto.

The instant invention contemplates that strain gauges 120a and 120b may be mounted on the exterior surface 114 of the sensor body 110, particularly, when the sensor 110 is adapted with the above described sleeve 150. In either form, the strain gauges 120a and 120b are sealed from environmental factors, particularly moisture, by any well known techniques, including but not being limited to sealed arrangement of the sensor body 110 and protective sleeve 150.

Figure 17:
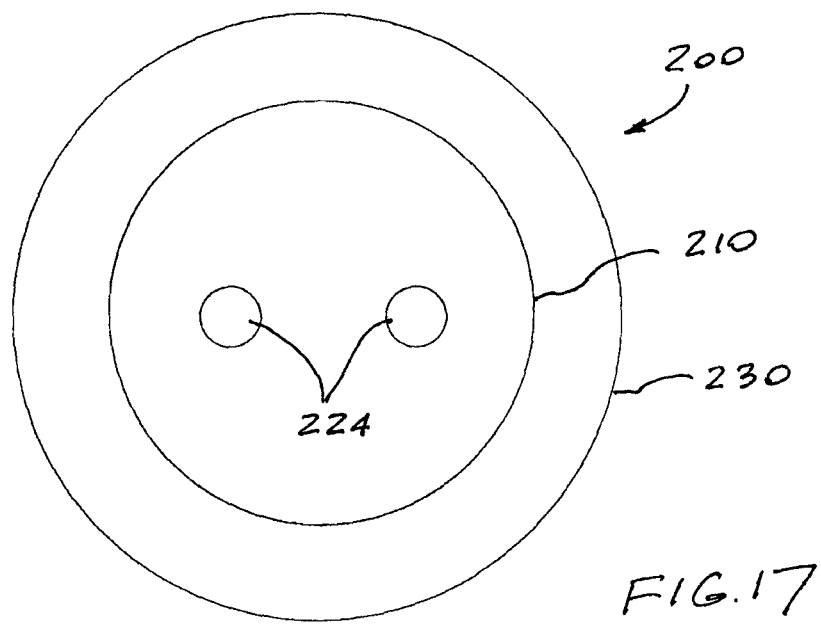
FIG. 17 is a planar end view of the sensor of FIG. 16.
Figure 16:
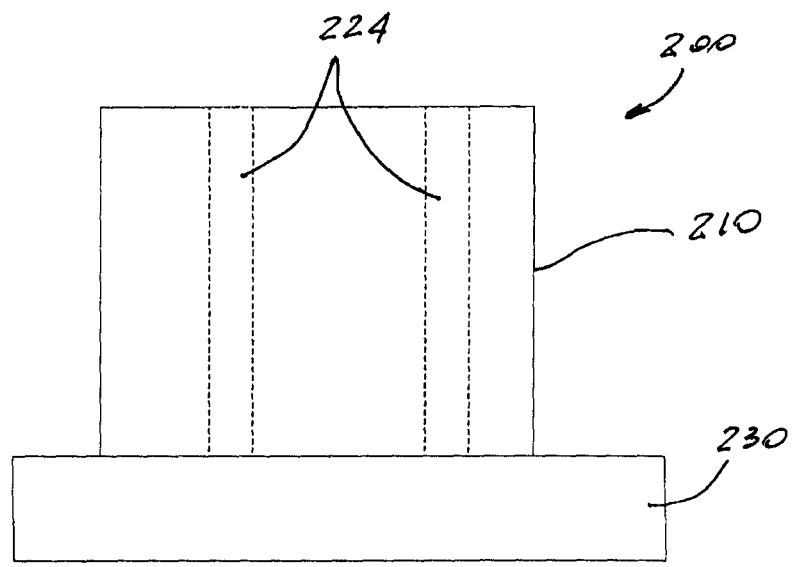
FIG. 16 is an elevation view of another alternative form of the sensor of FIG. 11.

FIGS. 11-17 illustrate additional forms of another embodiments of the invention wherein the sensor, generally designated as 200, comprises at least a pair of sensing elements, such as electrically conductive members or electrodes 220, either positioned on an exterior surface 212 of the sensor body 210 in a spaced apart relationship with each other, as best shown in FIGS. 11-14 or imbedded into the sensor body 210, as best shown by sensing elements 224 in FIGS. 16-17.

The sensor 200 in these forms measures the electrical resistance and impedance between one electrode 220 and the mixer itself (in case the mixer 10 is made of metal) or between spaced electrodes 220 that come in contact with the concrete mixture.

In the form of FIGS. 11-14, the sensor body 210 is preferably hollow and is manufactured from an electrically non-conductive material. The sensing elements include two ring-shaped electrically conductive members or electrodes 220 mounted in a spaced apart relationship with each other on an exterior surface 212 of the hollow sensor body 210 and wherein the sensor 200 further comprises a base 230 attached to one end of the hollow sensor body 210 and a control circuit 240 disposed within a hollow interior 232 of the base 230, the control circuit 240 being at least configured to generate and apply voltage to the two ring-shaped electrically conductive members 220 and measure a current between the two ring-shaped electrically conductive members 220, the current being indicative of at least one of a resistance and impedance of a concrete mixture contained within the mixer 10. It would be understood that the electrically conductive members 220 can be provided in other shapes to match the peripheral shape of the sensor body 210. The sensor body 210 may be further provided with apertures 211 so as to physically connect electrical wires (not shown) from the control circuit 240 to the electrically conductive members 220, wherein the electrically conductive members 220 are ultimately coupled to a processor within the control circuit 240.

The control circuit 240, at least contains the above described processor 142 and, in addition to programming the AC generator 250 to specific frequency and voltage, is configured to measure the current consumed by the AC generator 250 (being a frequency generator or a sine wave), measure the voltage between the inner rings 220, calculate the resistance of the concrete based on the formula R=V/I, determine if the sensor body 210 is submerged in the concrete mixture or out of the concrete mixture, determine the location of the sensor 200 by using measurements from an optional accelerometer 170, and determine the entry and departure angles of the sensor 200. The control circuit 240 is further being either configured to calculate the slump and the volume of the concrete mixture based on the angles values and the water to cement ratio based on the resistance or transmit all relevant data to the computer processing unit 12 that will calculate the slump and the volume of the concrete mixture based on the angles values and the water to cement ratio based on the resistance and make any adjustments to the concrete mixture within the mixer 10 as/if required. It must be noted that the computer processing unit 12 may be configured to incorporate the control circuit 240 or the previously described control circuit 140.

It is presently preferred that the sensor body 210 is hollow and is manufactured from an electrically non-conductive material and wherein the sensing elements include four ring-shaped electrically conductive members 200 mounted in a spaced apart relationship with each other on the exterior surface 212 of the hollow body 210. The sensor 200, in this form, also includes the above described base 230, preferably with the mounting apertures 231, and being preferably connected to the sensor body 210 by the above described rigid connection. Further, the control circuit 240 is preferably disposed within the hollow interior 232 of the base 230 and further includes the programmable AC generator 250 disposed within the hollow interior 232 of the base 230. The programmable AC generator 250 being operatively coupled to the control circuit 240 and to outer electrically conductive members 220. Further, two inner electrically conductive members 220 are operatively coupled to the control circuit 240, wherein the control circuit 240 is configured to program the programmable AC generator 250, measure a current generated by the programmable AC generator 250 and measure a voltage between the inner conductive members 220.

Although the voltage can be measured between the outer electrically conductive members 220, it has been found that some of the current will drift and the measured resistance is the combined resistance of the concrete mixture and additional noise. When the voltage is measured on the inner conductive members 220 and the current is known from feeding circuit, then it has been found that the voltage measured is only on the resistance of the concrete mixture.

In either embodiment, the electrical resistance is measured both in DC and in AC (in varying frequencies) the result is a spectrum of electrical resistances. The sensor 200 also measures the phase shift of the AC signal to measure the impedance.

The measurement is done while the mixer 10 is rotating and the sensor 200 travels along the circumference of the mixer 10 and measures the resistance/impedance. Once the sensor 200 is submerged into the concrete mixture, there is a huge reduction the electrical resistance as measured by the electrically conductive members 220. So the sensor 200 can distinguish between measurements done inside the concrete mixture and those outside the concrete mixture.

By using an accelerometer 170, the system can identify where the sensor 200 was submerged into the concrete mixture and where it went out of the concrete mixture. The analysis of both locations will give two angles as measured from the highest point of the sensor, entry angle ($\alpha 1$) and leave angle ($\alpha 2$) the difference between the two angles has direct correlation to the slump of the concrete mixture, and the average between the two angles has a direct correlation to the level of the concrete mixture in the mixer 10 and from there to the volume of the concrete mixture.

The presently preferred method of determining volume and slump is based on using sensor 200 to measure electrical resistance and is further based on finding the locations of the sensor 200 entering and leaving the concrete by measuring the total revolution time (T1), the total submerged time (T2), the time elapsed from the point the sensor 200 was at the highest point and the time it submerged into the concrete (T3) and the time elapsed since it went out of the concrete until it came back to the highest point (T4). Identifying the highest point can be done by using a simple weight attached to a load cell either vertically or horizontally, there are two points where the load cell will have the same value, at the top and at the bottom (this value can be obtained during a simple calibration process of mounting the sensor vertically and measuring the force applied on the load cell by the weight), the electrical resistance will determine if the sensor 200 is at the lowest point (submerged) or at the highest point (out of the concrete), if the sensor can't identify that it means the mixer is empty (the identification of this status will be used for identifying if the pouring process is over. Accordingly, the volume and slump can be calculated as follows:

$$\alpha 1 = \text{Entry\_Angle}$$

$$\alpha 2 = \text{Exit\_Angle}$$

$$\text{Volume} = f(\alpha 1 + \alpha 2)$$

$$\text{Slump} = g(\alpha 2 - \alpha 1)$$

$$W/C = w(R)$$

wherein:
f=function
g=function
W=Water
C=Cement
w=function
R=resistance

Functions f, g, and w can be obtained from translations tables developed, for example, by historical measurements.

In case we do not use an accelerometer and just use simple time calculations, the angles can be calculated in the following manner:

$$\alpha 1 = (T\tfrac{1}{2} - T3)/(T\tfrac{1}{2}) * 180$$

$$\alpha 2 = (T\tfrac{1}{2} - T4)/(T\tfrac{1}{2}) * 180$$

The invention also contemplates use of predefined conversion tables, obtained during a calibration process, instead of using the above functions.

Figure 18:
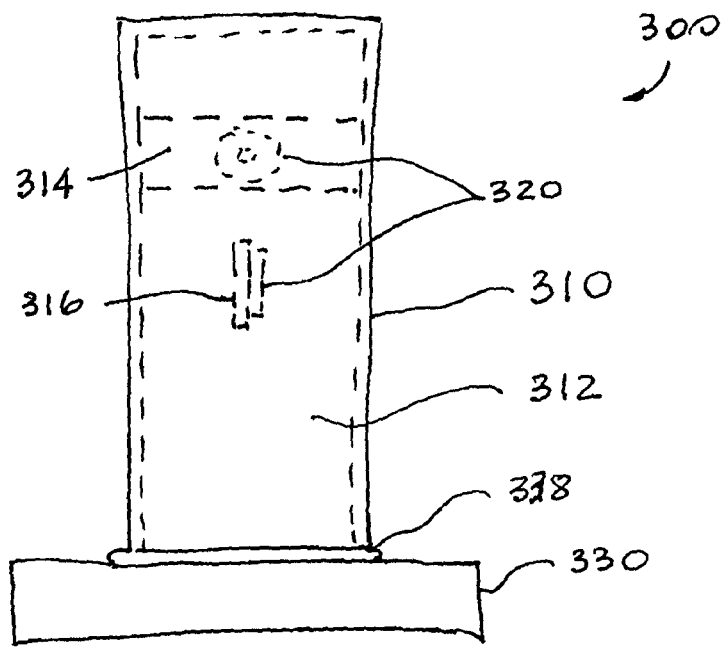
FIG. 18 is a diagrammatic elevation view of one form of a further embodiment of a sensor for sensing concrete mixture within a rotating mixer of FIG. 1.

In yet another embodiment of FIG. 18, the invention provides a sensor, generally designated as 300, that includes a sensor body 310 having a hollow interior 312. The sensor 300 further includes a pair of pressure type load cells 320 mounted within the hollow interior 312 to measure forces in two directions, being generally perpendicular to each other. By way of one example only, the body 310 is provided as a hollow body and the sensor 300 further includes a pair of braces 314, 316 having each end thereof connected to the inner surface of the hollow body 310 but oriented generally perpendicular to each other.

The sensor 300 preferably includes a base 330 that is connected to one end of the body 310 by way of a flexible connection 338 allowing movement of the body 310 relative to the base 330. Such flexible connection could be of the type, for example as disclosed in U.S. Pat. Pub. Number 2012/0204625 to Beaupre et al.

Figure 19:
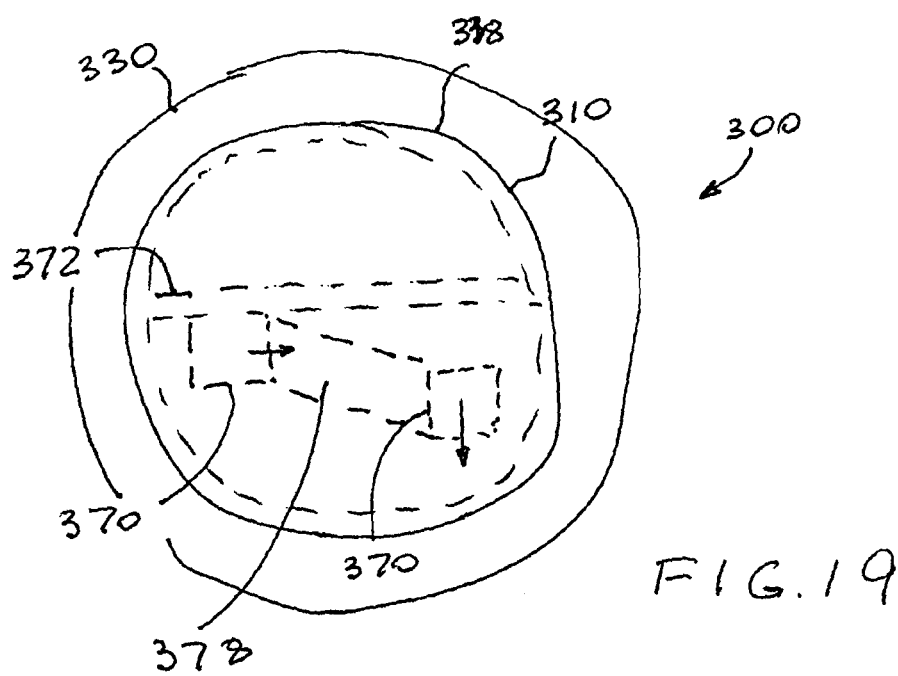
FIG. 19 is a diagrammatic planar view of another form of the further embodiment of a sensor for sensing concrete mixture within a rotating mixer of FIG. 1.

In an alternative form of FIG. 19, the pair of sensing elements may be provided as beam load cells 370. Each beam load cell 370 will be mounted on the base 330, however, one of the two beam load cells will be also connected to a brace 372, while the second beam load cells 370 will be free standing on the base 330. The beam load cells 370 are also connected therebetween with a flexible connection that may be the above described flexible connection 338.

It would be understood that the instant invention can be configured with use of two sensors 300, each containing a single pressure type load cell 20 or a single beam load cells 370, wherein the sensors 300 are so mounted that each sensor 300 senses force in a distinct direction.

The reader is advised that the above described sensor 300 may be employed with the above described protective sleeve 150.

Furthermore, the method of measuring volume and slump of the concrete mixture with sensor(s) 300 is generally identical to a method employing the above described sensor (s) 100.

In the conventional mixing process, with either one of the above described embodiment, the mixer 10 is required to idle and count the mixer revolutions to attempt to achieve a consistent mixture. The present invention allows the user to charge the mixer 10 and leave the yard, monitoring of the slump and the electrical characteristics over several revolutions. The deviation from the average will indicate if the material is well mixed, the lower the deviation is the better the mix is mixed. Similarly comparison of this data to data obtained from "standard" or baseline batch configuration will indicate if this batch is similar to the "standard" batch.

Further, the change in the mix volume and the start and stop time of the change in volume are recorded. Thus, the user of the present invention will know the amount of concrete mixture poured, as well as the time of the pour, thus preventing a financial loss through unauthorized pours. The user may also receive an alert as to the need to recharge the mixer 10.

While a presently preferred and various alternative embodiments of the present invention have been described in sufficient detail above to enable a person skilled in the relevant art to make and use the same it should be obvious that various other adaptations and modifications can be envisioned by those persons skilled in such art without departing from either the spirit of the invention or the scope of the appended claims.

INDUSTRIAL USE

The invention has industrial use in the concrete production industry.

I claim:

1. A sensor for a concrete mixer, said sensor comprising:
    (a) a hollow body having an interior and an interior surface; and
    (b) sensing elements mounted within said interior of said hollow body and connectable to a control circuit; said sensing elements being mounted such that the sensor, when attached to a wall of the concrete mixer such that the sensor moves through a concrete mixture, is configured to measure, during a movement of the sensor through the concrete mixture, a first force along a first axis being parallel to a rotation direction of the concrete mixer and to measure, during the movement of the sensor through the concrete mixture, a second force along a second axis disposed at an angle to the first axis, the second axis being defined by a movement of a mixing helix within the concrete mixer.

2. The sensor of claim 1, wherein said sensing elements comprise two strain gauges, one of said two strain gauges is mounted on said interior surface to measure said first force along said first axis and another one of said two strain gauges is mounted on said interior surface to measure said second force along said second axis.

3. The sensor of claim 1, wherein said sensing elements include four strain gauges mounted on said interior surface of said hollow body and wherein two of said four strain gauges are mounted, mediate ends of said hollow body, along said first axis to measure said first force and remaining two strain gauges are mounted along said second axis to measure said second force.

4. The sensor of claim 3, wherein said sensor further comprises a base attached to one end of said hollow body and said control circuit being disposed within a hollow interior of said base, said control circuit including a processor and wherein said four strain gauges are connected with wires to said processor in a Wheatstone bridge arrangement.

5. The sensor of claim 1, wherein said sensor further includes a base, a flexible connection between said base and one end of said hollow body and two brace members mounted, generally perpendicular to each other, within said interior of said hollow body wherein each end of each brace member is attached to said interior surface of said hollow body; wherein said sensing elements include a pair of pressure load cells, and wherein one of said pair of pressure load cells is mounted on one of said two brace members to measure said first force and another one of said pair of pressure load cells is mounted on another one of said two brace members to measure said second force.

6. The sensor of claim 1, wherein said sensor further includes a base, a flexible connection between said base and one end of said hollow body and a brace member having each end thereof attached to said interior surface of said hollow body; wherein said sensing elements include a pair of beam load cells connected therebetween and further connected to said base and extending into said hollow body, and wherein one of said pair of beam load cells is further connected to said brace member; whereby said sensor is configured to measure said first force and measure said second force.

7. A sensor for a concrete mixer, comprising:
    (a) a hollow body having an interior and an interior surface;
    (b) sensing elements mounted within said interior of said hollow body and connectable to a control circuit, said sensing elements being mounted such that the sensor, when attached to a wall of the concrete mixer such that the sensor moves through a concrete mixture, is configured to measure, during a movement of the sensor through the concrete mixture, a first force along a first axis being parallel to a rotation direction of the concrete mixer and to measure, during the movement of the sensor through the concrete mixture, a second force along a second axis disposed at an angle to the first axis, the second axis being defined by a movement of a mixing helix within the concrete mixer; and
    (c) a sleeve, including:

i. a first layer surrounding an exterior surface of said hollow body and being manufactured from a first material, ii. a second layer surrounding an exterior surface of said first layer and being manufactured from a second material, and iii. wherein said second material has a hardness thereof being greater than a hardness of said first material.

8. The sensor of claim 7, wherein said hardness of said second material is sufficient to resist a wear of said second material layer from a contact with a concrete mixture.

9. The sensor of claim 7, wherein said hardness of said second material is sufficient to cushion shocks during a movement of said sensor through a concrete mixture and to reduce a noise factor therefrom while allowing said sensor to measure rheological characteristics of the concrete mixture.

10. A system for measuring rheological properties in a concrete mixer, comprising:
(a) one or more rheological sensors, each including a hollow body thereof disposed within a hollow interior of the concrete mixer and one or more sensing elements mounted within an interior of said hollow body;
(b) a control circuit connected to said one or more sensing elements; and
(c) whereby said rheological system is configured to measure, when said one or more rheological sensors are attached to a wall of the concrete mixer and rotate with the concrete mixer, a first force along a first axis being parallel to an axis of rotation of said concrete mixer and further measure a second force along a second axis being disposed at an angle to said first axis, said second axis defined by a movement of a mixing helix within the concrete mixer.

11. A sensor for a concrete mixer, said sensor comprising:
(a) a body comprising an electrically non-conductive material;
(b) a base comprising a hollow interior;
(c) a rigid connection between said base and one end of said body;
(d) a control circuit disposed within said hollow interior of said base;
(e) a programmable AC generator disposed within said hollow interior of said base, said programmable AC generator operatively coupled to said control circuit;
(f) four electrically conductive members mounted in a spaced apart relationship with each other along a length of said body on an exterior surface thereof, two outer electrically conductive members from said four electrically conductive members connected to said programmable AC generator, two inner electrically conductive members from said four electrically conductive members connected to said control circuit; and
(g) wherein said control circuit is at least configured to program said programmable AC generator, measure a current consumed by said programmable AC generator and measure a voltage between said two inner electrically conductive members during a movement of the sensor through a concrete mixture.

12. A sensor for a concrete mixer, said sensor comprising:
(a) a hollow base;
(b) a control circuit mounted within the hollow base;
(c) a hollow body having one end thereof coupled to the hollow base, the hollow body comprising an interior surface; and
(d) sensing elements mounted on the interior surface of the hollow body and connected to the control circuit;
the sensing elements comprise four strain gauges mounted on the interior surface of the hollow body such that when the sensor is attached to a wall of a concrete mixer, two of the four strain gauges are mounted along a first axis parallel to a rotation direction of the concrete mixer, and the other two of the four strain gauges are mounted along a second axis, said second axis being generally perpendicular to the first axis, as defined by a movement of a mixing helix within the concrete mixer;
the sensing elements being mounted such that the sensor, when attached to a wall of the concrete mixer such that it moves through a concrete mixture, is configured to measure a first force along the first axis parallel to the axis of rotation of the concrete mixer and to measure a second force along the second axis disposed at the angle to the first axis, the second axis being defined by the movement of the mixing helix within the concrete mixer.

13. The sensor of claim 11, wherein said circuit is further configured to measure entry and exit angles of said one or more sensors into and from said aggregate concrete mixture.

14. The sensor of claim 13, wherein said circuit is further configured to determine at least one of a volume and a slump of the aggregate concrete mixture based on said measurement of entry and exit angles of said sensor into and from the aggregate concrete mixture.

* * * * *